(12) United States Patent
Delia

(10) Patent No.: US 9,955,877 B2
(45) Date of Patent: May 1, 2018

(54) WEARABLE WIRELESS DEVICE APPLICABLE TO THE HAND OR FOOT, WIRELESS SYSTEM INCLUDING THE DEVICE AND METHOD FOR REDUCING THE RISK OF DIFFERENT CRITICAL SITUATIONS OF HYPOXIA AND/OR BRADYCARDIA

(71) Applicant: Diego Alejandro Delia, Ciudad Autonoma de Buenos Aires (AR)

(72) Inventor: Diego Alejandro Delia, Ciudad Autonoma de Buenos Aires (AR)

(*) Notice: Subject to any disclaimer, the term of this patent is extended or adjusted under 35 U.S.C. 154(b) by 47 days.

(21) Appl. No.: 14/959,383

(22) Filed: Dec. 4, 2015

(65) Prior Publication Data

US 2016/0262637 A1    Sep. 15, 2016

Related U.S. Application Data

(60) Provisional application No. 62/130,938, filed on Mar. 10, 2015.

(51) Int. Cl.
*A61B 5/1455*    (2006.01)
*A61B 5/0205*    (2006.01)
(Continued)

(52) U.S. Cl.
CPC ...... *A61B 5/02055* (2013.01); *A61B 5/02416* (2013.01); *A61B 5/14551* (2013.01); *A61B 5/14552* (2013.01); *A61B 5/4818* (2013.01); *A61B 5/6825* (2013.01); *A61B 5/6829* (2013.01); *A61B 5/7271* (2013.01);
(Continued)

(58) Field of Classification Search
CPC .............. A61B 5/02438; A61B 5/0295; A61B 5/14551; A61B 5/6829; A61B 5/746; A61B 2503/04
See application file for complete search history.

(56) References Cited

U.S. PATENT DOCUMENTS 6,047,201 A    4/2000    Jackson, III
6,811,538 B2    11/2004    Westbrook et al.
(Continued)

OTHER PUBLICATIONS

Chilean Office Action issued in counterpart Chilean Application No. 201600505 dated May 29, 2017 (seven pages).
(Continued)

*Primary Examiner* — Tammie K Heller
(74) *Attorney, Agent, or Firm* — Crowell & Moring LLP

(57) ABSTRACT

A wearable, wireless, non-invasive device applicable to the hand or foot, a wireless system, and a method for reducing the risk of different critical situations of hypoxia and/or bradycardia possibly occurring in victims of sudden infant death syndrome (SIDS), Pierre Robin Sequence patients, preterm babies, and adults, and for the prevention of the sleep apnea, is based on use of a sensor and a computing algorithm sufficient to reduce false alarms and save lives. The device is worn on the hand or foot of a user. Part of the device may be placed on the proximal phalange of a finger or a foot, or even in the palm. The electronics of the device may be placed inside gloves or booties of different sizes to accommodate the hands or feet of different wearers. The device measures blood oxygen saturation and heart rate through a sensor that is preferably a pulse oximeter.

8 Claims, 8 Drawing Sheets

(51) Int. Cl.
*A61B 5/00* (2006.01)
*A61B 5/024* (2006.01)

(52) U.S. Cl.
CPC ............ *A61B 5/742* (2013.01); *A61B 5/7455* (2013.01); *A61B 5/746* (2013.01); *A61B 2503/04* (2013.01)

(56) References Cited

U.S. PATENT DOCUMENTS

| | | |
|---|---|---|
| 8,620,448 B1 | 12/2013 | Delia |
| 8,981,926 B2 * | 3/2015 | Al-Ali .................. A61B 5/7455 340/539.12 |
| 2010/0099963 A1 | 4/2010 | Kilger |
| 2011/0004072 A1 | 1/2011 | Fletcher et al. |
| 2011/0208539 A1 | 8/2011 | Lynn |
| 2013/0116514 A1 | 5/2013 | Kroner et al. |
| 2013/0178718 A1 | 7/2013 | Tran et al. |
| 2016/0262637 A1 | 9/2016 | Delia |

OTHER PUBLICATIONS

English translation of document CL (Chilean Office Action issued in counterpart Chilean Application No. 201600505 dated May 29, 2017) previously filed on Jun. 28, 2017 (10 pages).

\* cited by examiner

WEARABLE WIRELESS DEVICE APPLICABLE TO THE HAND OR FOOT, WIRELESS SYSTEM INCLUDING THE DEVICE AND METHOD FOR REDUCING THE RISK OF DIFFERENT CRITICAL SITUATIONS OF HYPOXIA AND/OR BRADYCARDIA

This application claims priority under 35 U.S.C. 119(e) to prior U.S. provisional application No. 62/130,938, filed Mar. 10, 2015, the entire disclosure of which is incorporated herein by reference.

BACKGROUND OF THE INVENTION

The present invention reveals a wearable, wireless, non-invasive device applicable to the hand or foot, a wireless system and method for reducing the risk of different critical situations of hypoxia and/or bradycardia that could happen in the sudden infant death syndrome (SIDS), Pierre Robin Sequence patients, preterm babies and adults and for the prevention of the Sleep Apnea. The device is based on the use of a sensor and a computing algorithm sufficient to reduce false alarms and save lives. The device is worn on the hand or foot of the user. Part of the device may be placed on the proximal phalange of a finger or a foot, or even in the palm. The electronics of the device may be placed inside gloves or booties of different sizes to accommodate the hands or feet of different wearers. The device measures blood oxygen saturation and heart rate through a sensor that is preferably a pulse oximeter. The device is designed to first monitor if non-zero numeric values of heart rate or blood oxygen saturation are measured. If this is not verified it will assume the device is not working correctly or is placed off its correct position. When either measured blood oxygen saturation values or heart rate are detected and falls below certain assignable and pre-adjusted thresholds, a complex algorithm is activated. This algorithm activates specific timers which are able to measure elapsed time of periods during which the device detects values below threshold for blood oxygenation values and/or heart rate. If either heart rate or blood oxygenation is found to be at a pathological level (that is below or above certain thresholds) for a period longer than a preset safety trigger delay of the timer, an electric discharge is delivered to stimulate the wearer's reaction and a local and/or remote alarm occurs. These alarms can be received in devices such as smartphones or remote computers. The future miniaturization of this device could allow making the device as small as a ring, with the electrodes disposed around the finger. Also the device can fit in a wrist band, with the electrodes disposed in some region of the wrist.

1. Field of the Invention

Sudden Infant Death Syndrome (SIDS) is defined as the sudden and unexpected death of an infant of less than 1 year who otherwise seems to be healthy. It is also known as "infantile sudden death syndrome," "cradle death," or "white death." The infant is generally found dead after having put him/her to bed, with no signs of having suffered any stress or health disorder. The present invention allows early detecting a lack of blood oxygenation and causing the user, after a predefined delay, to react instinctively in order to correct the low blood oxygenation detected, and also to generate an alarm signal before the infant enters a critical risk situation. If the remote alarm feature of the device is activated by the caregiver, the device will wirelessly send an alarm signal to a tablet or smartphone of the caregiver as well. The alarm signal may be set to occur after a predefined time period after the detection of falling heart rate and/or blood oxygen levels.

Sudden Infant Death Syndrome (SIDS) is one of the leading causes of death among infants one month through one year of age in the United States. The National Institute of Child Health and Human Development (NICHD) defines SIDS as the sudden death of an infant under one year of age which remains unexplained after a thorough case investigation, including performance of a complete autopsy, examination of the death scene and review of the clinical history. SIDS is a diagnosis of exclusion, assigned only once all known and possible causes of death have been ruled out. SIDS claims the lives of almost 2,500 infants in the US each year—that is nearly 7 babies every day. SIDS deaths occur unexpectedly and quickly to apparently healthy infants, usually during periods of sleep. It is not caused by suffocation, choking, or smothering. It occurs in families of all races and socioeconomic levels. SIDS cannot be predicted or prevented and can claim any baby, in spite of parents doing everything right.

Currently, there is no theory for SIDS that describes a lack of response to pain. The present invention uses pain sensitivity to address the risk of SIDS. Detection of a reduced heart rate is of utmost importance, being an event that may occur in multiple potentially life threatening situations, and perhaps in SIDS too. Although not confirmed, it can be assumed that before the child dies, he/she will suffer hypoxia (reduced blood oxygen saturation) and/or bradycardia (reduced heart rate).

There is another group or people that could benefit from the device of the present invention. Sudden Unexplained Death in Childhood (SUDC) occurs from 1 year of age through adolescence. It is far less common than SIDS, but, like SIDS, it is also defined by an inability to identify a cause of death after a complete autopsy or death scene investigation.

Other groups of risk:
Pierre Robin Sequence babies who should not sleep looking up due to the risk of suffering hypoxia caused by the obstruction to breathing pathways due to the congenic lower jaw malformation.
Preterm babies due to the high risks caused by their delayed neuronal development.
Sudden Unexpected Infant Deaths (SUID).
Adults that attempt to sleep more safely, in which case other housings can be used such as those placed on the wrist or in a ring. For example, patients who underwent surgery and must sleep looking upwards, and particularly if they have overweight, show an increased risk of suffering hypoxia.
Wearers that want to prevent from falling asleep (no need of oxygen sensor, just heart rate sensor that could include heart rate variability measurement).

The present invention is based on the use of an algorithm combined with a sensor measuring blood oxygen saturation and heart rate, and for this purpose, in a highly preferred embodiment, a pulse oximeter is employed.

The pulse oximeter is a medical device that indirectly measures oxygen saturation in the patient's blood, as opposed to the direct measurement of oxygen saturation on a blood sample, and it also measures the heart rate. The pulse oximeter is usually connected to a medical monitor so that the healthcare staff may check the patient's oxygenation and heart rate at all times. Those which are battery-operated are portable, allowing to measure oxygen saturation outside the hospital or on an outpatient basis.

The pulse oximeter is a highly convenient and non-invasive measuring device. There are many different ways to measure the pulse oximetry. It usually has two small light emitting diodes (LEDs) facing a photodiode through a translucent portion of the patient's body, generally a finger or toe, or an earlobe. One of the LEDs is red, with a wavelength of 660 nm, and the other is infrared, at 905, 910, or 940 nm. Absorption of these wavelengths is very different between oxyhemoglobin and its deoxygenated form, therefore, from the red/infrared light absorption ratio, the difference between oxyhemoglobin and deoxyhemoglobin may be calculated. Oxyhemoglobin and deoxyhemoglobin absorbance is the same (isosbestic point) at 590 and 805 nm; the first oximeters used these wavelengths for the correction of hemoglobin concentration. As mentioned before, another very important function of these sensors is to measure the patient's heart rate, which is also used in the present invention to detect a reduction in the heart rate and wake up the patient, and to prevent the sudden infant death syndrome. Pulse oximetry can be performed in another way, the reflection. In reflection pulse oximetry, the only difference lies in the fact that the photodiode is on the same side as the LEDs. There are new methods more sophisticated that can measure under motion and low perfusion.

2. Description of Related Art

The following documents that refer to similar inventions were located:

U.S. Pat. No. 6,047,201 describes a device to help a caregiver monitor an infant to discover the onset of a Sudden Infant Death Syndrome event and to intervene to prevent the Sudden Infant Death Syndrome event. A foot and ankle wrap containing rechargeable batteries and a radio transmitter is connected to a toe cap containing a pulse oximeter by adjustable cords. Blood oxygen and pulse readouts from the pulse oximeter are transmitted to a monitor kept by the caregiver. Visible readouts of the blood oxygen and pulse are shown on the monitor for continuous view by the caregiver. The monitor sounds an alarm if the infant's blood oxygen drops to a dangerous level for predetermined period. The time delay prevents false alarms, therefore, provides a greater degree of alertness to the caregiver using the device. When not in use the device is recharged on a stand.

U.S. Pat. No. 8,620,448, of the same applicant as the present document, describes a non-invasive, wireless, portable device which is applicable to the finger in order to reduce the risk of the sudden infant death syndrome and to reduce the risk of apnea, slower heart rate, and heart arrest in all age groups. The device is placed tightly on the distal end of a user's finger. As it is placed on the finger, this device may be inside a fabric cap attached to a glove of different sizes. This device measures blood oxygen saturation and heart rate through a sensor that is preferably a pulse oximeter. When any of these parameters falls below certain user-predetermined thresholds, an electric discharge is delivered to stimulate the user's reaction and a local and/or remote alarm is fired. In certain applications, the device is adequate to make the sleeping user react, and in others to prevent the user from falling asleep.

DETAILED DESCRIPTION OF THE INVENTION

The present invention refers to a wearable, wireless, non-invasive device in a garment which is applied to a hand or foot in order to reduce the risk of different critical situations of hypoxia and/or bradycardia. These situations can happen in the Sudden Infant Death Syndrome, Pierre Robin Sequence babies, adults with sleep apnea, wearers who, due to particular requirement might have the need to sleep facing upwards, thus having a tendency of suffering hypoxia while sleeping.

The present invention consists of a wearable, wireless, non-invasive device that is placed on the hand or foot of the wearer and which measures blood oxygen saturation and heart rate by means of a pulse oximeter contained therein. In an embodiment of this invention, in which wearers use it when being asleep, as soon as any of these physiological parameters is detected to be out of a patient-predetermined range, the device activates a complex algorithm that turns on specific timers. After the algorithm considers the moment to act on the user, it releases a slight electric discharge on some part of the palm of hand or foot, depending on the placement of the device, making the wearer react to that stimulus while sleeping, interrupting the sleep cycle and allowing the wearer to put an end to the apnea episode or normalizing the heart rate.

Figure 1:
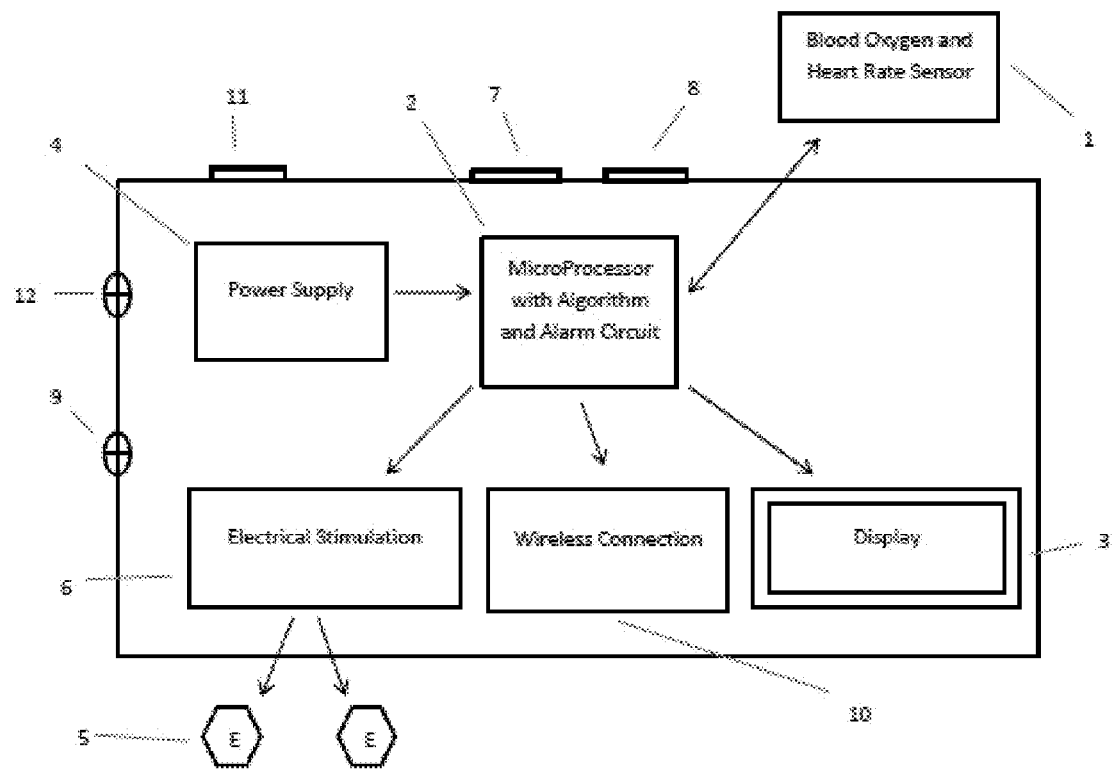
FIG. 1 is a basic block diagram of a typical portable pulse oximeter, and stimulus generator.

With reference to FIG. 1, a typical pulse oximeter is formed by a blood oxygen sensor 1 sending measurement signals to a microprocessor circuit 2. Circuit 2 contains the logic and the algorithm circuits that handle the measurement signals and sends the result to a display 3, which shows the resulting numeric values or no data. The display numerically shows the instant value for the blood oxygen content (measured as a percentage of the maximum value, e.g. 97-100% for a normal measurement) and heart rate (in beats per minute). The internal circuits of an oximeter are typically electrically supplied 4 by rechargeable batteries (generally AAA-sized or any other battery size appropriate for a portable and small apparatus). There is an ON/OFF/Stand By button 11.

Figure 5:
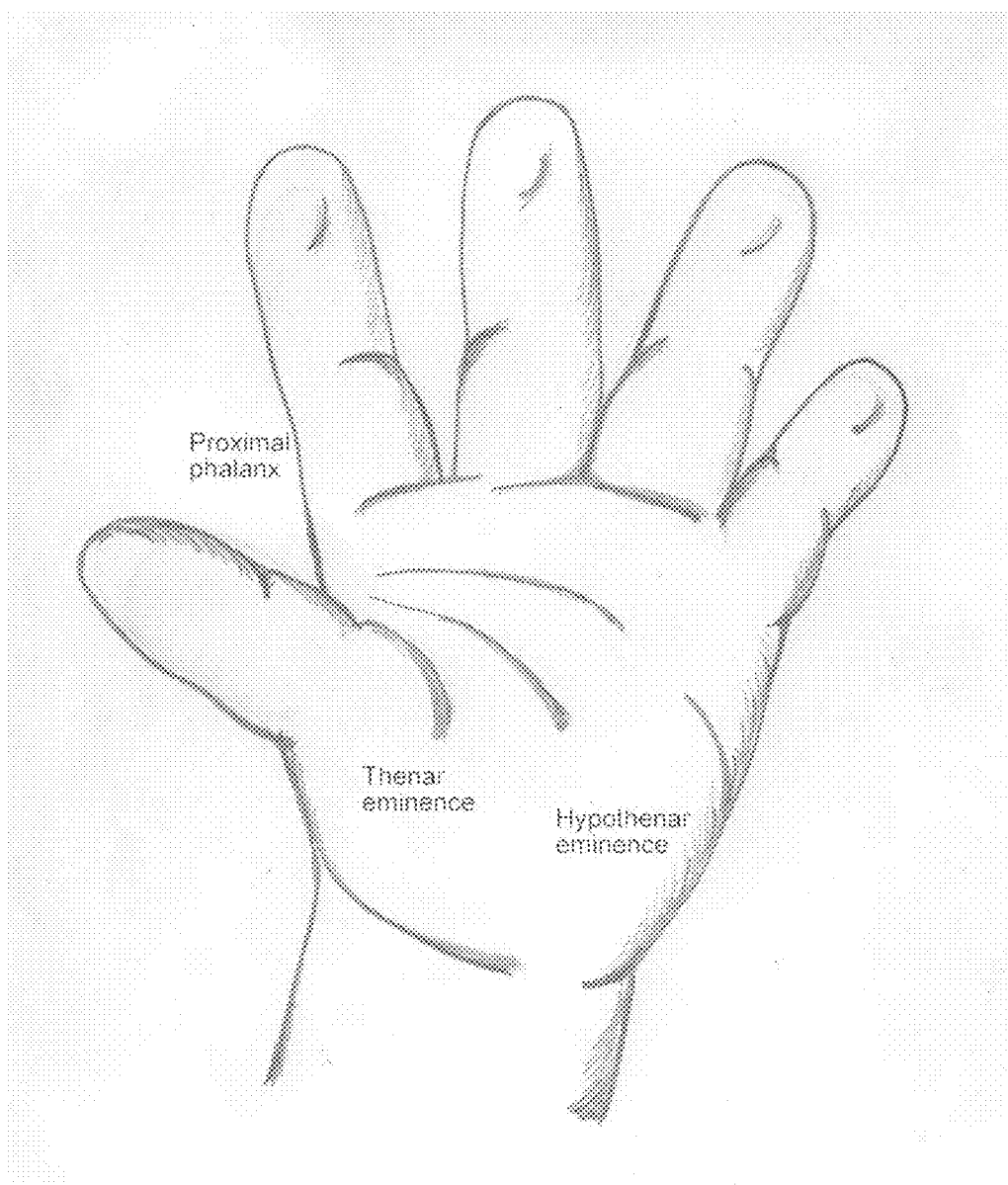
FIG. 5 is an image of a hand showing some locations.
Figure 7:
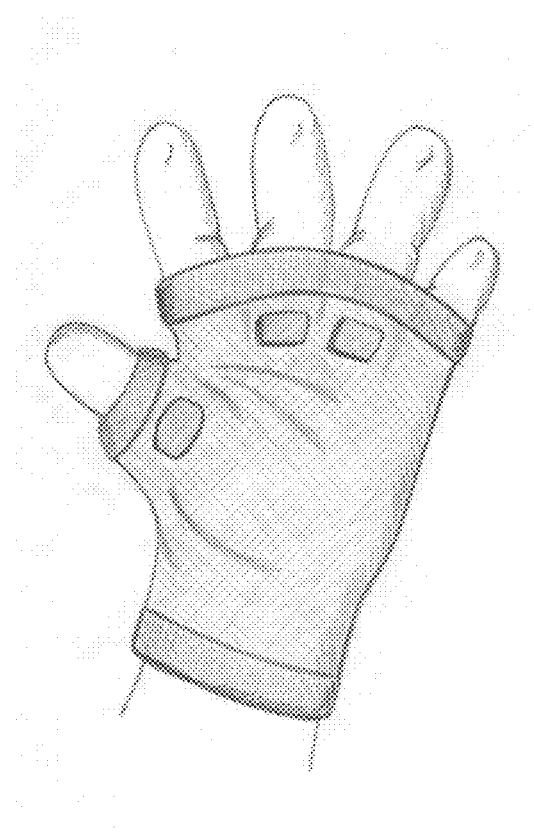
FIG. 7 describes a suitable housing for an infant.
Figure 8:
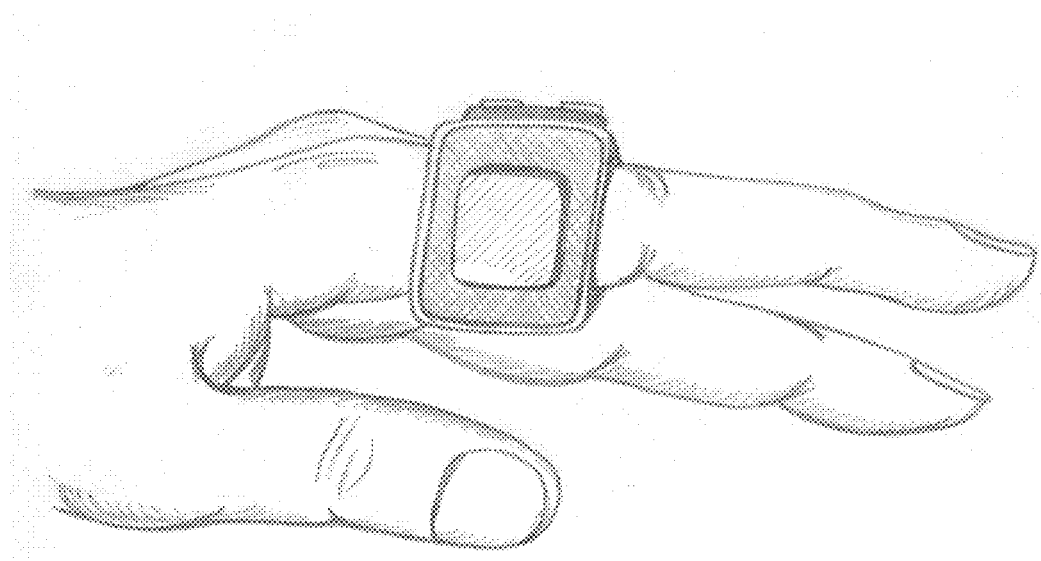
FIG. 8 describes a housing as a ring.
Figure 9:
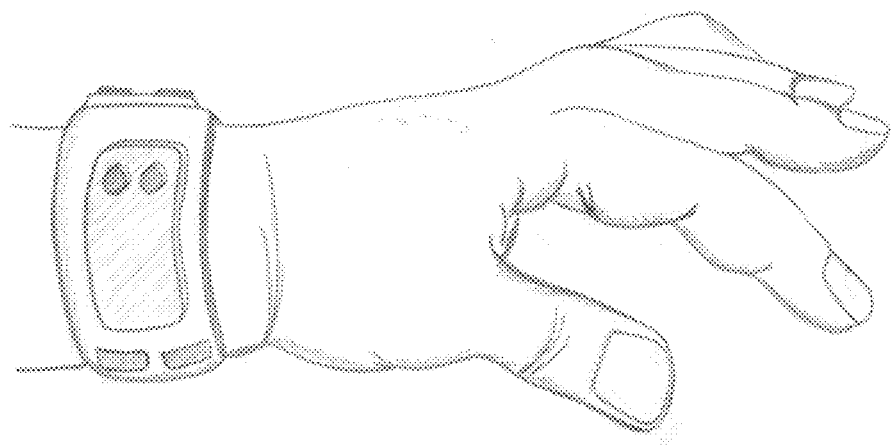
FIG. 9 describes a housing as a wrist band.

It may be seen that the complete device is formed by the following elements, represented by the block diagram of FIG. 1: a block section formed by almost all the typical elements that form a pulse oximeter, i.e., a blood oxygen saturation sensor and a heart rate meter 1, a measurement and display driver circuit 2, and a display 3 showing the numeric results. The circuit comprises means for measuring the current to be delivered to the pair of electrodes 5 through the electrical stimulus generator 6. This circuit is controlled by the microprocessor 2 and the values are shown in the display 3. Also, the block has a pair of metal electrodes 5 physically arranged on some location near the sensor 1, such as the thenar and hypothenar eminences (FIG. 5), or on the hand palm adjacent to the first finger phalanges (FIG. 7), or on a finger when the housing has the shape of a ring (FIG. 8), or on the wrist, when the housing has the shape of a wrist band (FIG. 9). These electrodes could be supported on the skin with some gel. The device also has a control and alarm-generating circuit 2 where the complex algorithm is located, an alarm display 3, which can be the same value display, a power supply 4, and an electric stimulation generator 6.

Block section forming part of a pulse oximeter (1, 2 and 3) are well known in the art and therefore will not be described in detail in this document. Display 3 may comprise a screen, a LED display, or any other technology appropriate for forming an alpha-numeric display.

The present invention also comprises a system formed by the safety device and remote wireless devices communicating with device. In the device the information can be shown on the display or may be also received by a Smartphone, a Tablet or any other suitable remote wireless electronic devices. The present device receives the oxygen level signal, i.e., oxygen saturation, and the heart rate signal from the measurement circuit block 2 and connects them to an algorithm control circuit and alarm-generating circuit 2. The control circuit 2 may consist of a pair of operational amplifiers that receive the signals and submit them to a feedback control loop with ON/OFF port, or else to an integrated circuit containing all these functions. Those skilled in the art will understand that any other circuit technology may be used to solve these functions, either in a totally analog way or with analogical/digital conversion. The user may modify the threshold oxygenation and/or heart rate levels and timers by pressing the push button 7 and 8 to adapt them to the requirements in each case. The control circuit will be adapted to modify its adjustment menu according to the signals received from the push button 7 and 8, in order to select the parameter to be adjusted with a single push button (for example, the adjustment parameter may be varied by pressing the push button for a certain amount of time in order to determine the adjustment of the oxygen saturation threshold, and for another certain amount of time to adjust the heart rate threshold). Also, in the system of the present invention, all the information such as the alarm thresholds, the timers, intensity (mA) values, duration of stimulus, kind of stimulus, etc., can be adjusted from the Smartphone or any other remote apparatus communicating to the safety device.

When the oxygen saturation sensor measures a level below the preset threshold, or if the heart rate falls below the preset threshold, the control circuit 2 will activate the complex algorithm and when considered appropriate, it will send a discharge order to the generator 6. In a simplified alternative embodiment, the block of control and alarm-generating circuit 2 and the block of electric stimulation generator 6 may be unified in a single integrated circuit designed for carrying out such actions.

When the wearer is sleeping the pulse oximeter can detect a drop in blood oxygen saturation and/or a sudden drop in heart rate, which is seen in display 3, as in any typical pulse oximeter. At the time of an oxygen desaturation below a predetermined limit, or at the time of a drop in heart rate, a complex algorithm is triggered to turn on specific timers. When any of these timers get the preset lapse of time necessary to activate, it will release activity to the electric stimulation generator block 6, which delivers an electric stimulus to the hand or foot through the two electrodes 5 placed, for example, on the thenar and hypothenar palm eminences or on the palm of the hand at a position near the fingers' lower portion (FIG. 7) or on a finger if the housing is on a ring (FIG. 8) or on the wrist if the housing is the wrist embodiment (FIG. 9), near the sensor 1 detecting the oxygen saturation signal. The recommended threshold values are well known by the skilled in the health area; for example, the user may set a safety threshold of less than 93% for oxygen saturation, and a minimum heart rate of 60 beats/minute, depending on the user. In the event the user does not shift his/her position to improve oxygen saturation and/or to reestablish heart rate, another electric discharge of equal value is delivered after 10 seconds, and so on, until the wearer returns to safe values. The skilled person could also have the possibility to send higher stimulus after the first given stimulus.

As already explained, the device may be placed inside different housings: a first embodiment formed by a ring (FIG. 8), containing a microprocessor a power source and all the rest of the components such as the oximetry and heart rate sensor, as well as the electrodes. This embodiment may be used in any finger but is recommended for adults only. It comprises a connection for power recharging and for connecting to another device if calibration is required.

As already explained, another housing embodiment foresees a wrist band (FIG. 9), comprising the microprocessor, the power source and all the rest of the components such as the oximetry and heart rate sensor, as well as the electrodes. It also comprises a connection for power recharging and for connecting to another device if calibration is required. This embodiment could be a new feature to be added in smart watches.

The device has the important option of continuously sending all the information data during the sleep to a virtual personal internet-based cloud service company. Also, it can send the information to a bigger cloud service company such as a healthcare company or hospital service facility in order collect data which should be extremely useful to continue studying the different patterns and etiology of the SIDS.

The device is designed to store in the internal memory all the patient's information such as the number of delivered stimuli, the pattern of the evaluated physiological parameters, dates, timing, etc. and send the information to be stored in a remote monitoring device.

The device is also designed to check the charging status of the batteries housed in it and also those housed in the remote monitoring device.

The device might be provided with an optional outlet alarm connector 9 (preferably USB) from which the discharge alarm can be remotely repeated through an optional cable which connects it to a safety monitoring apparatus. In an alternative low cost embodiment, the alarm display 3 may comprise a single LED that turns on to show an abnormal state or, in a more complete embodiment, through an alpha-numeric display indicating the occurrence of the abnormal state and further supplementary information, such as the type of problem, date and time of the alarm, etc. A further embodiment also foresees a simpler version in which there is no display and the information is totally monitored via the remotely connected device.

Figure 6:
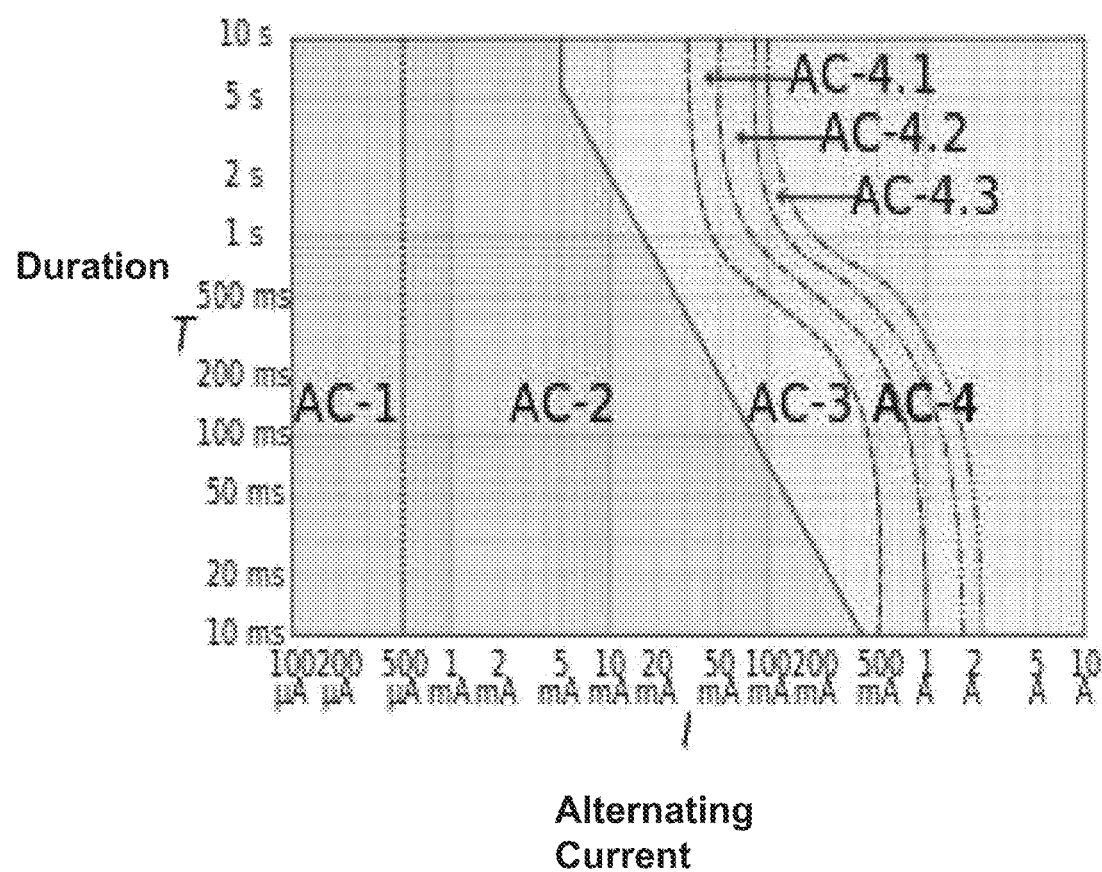
FIG. 6 describes effects of current on human beings.

The electric stimulation generator block 6 generates an electric stimulation signal that is weak enough so that the user's health is not compromised, but at the same time intense enough so as to make him/her react. The electrical current delivered by the electrodes will be safe and it will be in most cases within Zone AC-1 and in some cases in Zone AC-2, as shown in FIG. 6. FIG. 6 is a log-log graph of the effect of alternating current I of duration T passing from left hand to feet as defined in IEC publication 60479-1, redrawn based on Weineng Wang, Zhiqiang Wang, Xiao Peng, "Effects of the Earth Current Frequency and Distortion on Residual Current Devices", Scientific Journal of Control Engineering, December 2013, Vol 3 Issue 6 pp 417-422, where AC-1: imperceptible, AC-2: perceptible but no muscle reaction, AC-3: muscle contraction with reversible effects, AC-4: possible irreversible effects, AC-4.1: up to 5% probability of heart fibrillation, AC-4.2: 5-50% probability of fibrillation, and AC-4.3: over 50% probability of fibrillation.

This current design can be powered by any other suitable portable power source. The inventor is aware of the need of powering the device with a highly secure means and also the need to energize the circuitry with a very small power source. Batteries adequate for miniature devices such as those used in electronic wrist watches are highly preferable. The power voltage can range from 4.5 DCV to 18 DCV. An On/Off switch is supplied with a green LED to indicate that the unit is on. Three rotary switches are available: one rotary switch S2 will set the pulse frequency to 60, 250, 500, 750 Hz and 1 KHz. Switch S1 will select either a continuous pulse of 50% duty cycle of selected frequency or a 1 second pulse with 10% duty cycle. In the 10% duty cycle the second 7555 timer will generate the 60, 250, 500, 750 Hz, or 1 KHz pulse thus generating a single pulse per second. This stimulus signal resembles the one used in a multiple shock approach. To turn on the pulse the user push the pushbutton S4 and hold it pressed. There is also a red LED to indicate that the pulse is active. The switch S4 powers the timers 7556, therefore, no pulses are outputted if pushbutton S4 is not switched. This was designed and successfully tested in this way for acknowledging that the pulse stream is active. The other two rotary switches are for setting the output current in an easier way. The current range is set from 0.01 mA to 5.0 mA max. The schematic has notes how to use the current switches. A spreadsheet of the resistive ladder has been created and this has identified a less than 0.1% error for nominal resistive values. 0.1% tolerance resistors will be used. The current pulse with the op-amp has been simulated and prototype built to confirm the pulse works. The only new item is the resistive ladder which has also been simulated and the voltage is as expected. The frequencies and duty cycles mentioned in this paragraph are preferred values but the actual range of these might be broadened after further tests.

The current used in the electrical stimuli was thoroughly tested during May and June 2015 in 46 patients in an age range of 3 months to 76 years. The tests in newborns were carried out while they were asleep. It is important to point out that the results obtained were of great importance in the design of the present invention to correctly select the device's stimulus parameters and obtain safe and useful patient reaction. The test on newborns was first carried out on their parents to let them verify that the current stimuli are always harmless. These tests were indispensable for the correct design of the device of the present invention because this type of data is not available in the international bibliography, and particularly if related to babies and youngsters, because until now a test for finding out the minimum amperage for delivering a stimulus on a human hand or a foot was not interesting.

The first test on six babies in a range of 0-12 months of age resulted in values of 0.03 mA to 0.05 mA for obtaining a reaction. These values are well within the AC-1 safety zone (see FIG. 6). These babies while being asleep, when the stimuli were delivered reacted positively and afterwards kept on sleeping, except for one case that started crying and woke up. It was mostly surprising that all other tested patients did not react to these stimulus currents and required values in a range of 0.13 mA to 0.78 mA and these were delivered while being awake.

In children being 8 to 12 years old, while being asleep it was necessary to apply higher amperage values than those required when being awake; however the values never exceeded 0.74 mA.

Since no tests were carried out on sleeping adults, it is believed that the required amperage will have to be higher and, in order to keep within the safe values of the table of FIG. 6 and never exceed the AC-2 zone, even under a continuous discharge, a range of 0.01 mA to 5.0 mA was selected.

The caregiver will be free to vary the current signal by means of the push button 7 in order to adapt it to the user's age, weight, and condition.

The power supply 4 provides stable direct current to all circuits in the device. In a preferred embodiment, with the aim of enhancing portability, the power supply is replaced by a receptacle holding rechargeable batteries of suitable supply voltage. The device optionally has an alternative power input connector from an external 3V DC power supply in case the user does not have the required batteries. In a more developed embodiment, the power supply is a conventional regulated supply or, for a better miniaturization, a regulated switching power supply is used.

The electric discharge on the hand or foot produces a slightly painful stimulus, and the wearer responds with an immediate increase of the heart rate and/or oxygenation. If this does not happen, the electric discharge will be repeated 10 seconds later, and so on. Each electric discharge could be a single pulse or multiple pulses, of short or long duration (measured in milliseconds).

Also, this device may be monitored by a smartphone or computer through wireless connection or USB connection 9 or phone, and also implemented in pairs, that is, a set of two devices interconnected by wireless technology 10 or a cell phone, which is ideal in cases in which the user is a newborn or infant, who must be communicated with his/her parent or caregiver. In these cases, both devices receive the data of the child's heart rate and blood oxygen level and, therefore, in the event that any of these measured levels fall below normal values, this embodiment of the present invention foresees producing an electric discharge when the algorithm considers on both people, that is, the patient and the caregiver. The alarm received by the caregiver could be audible and/or stimulation if it used in pairs and this arrangement will cooperate to ensure that the caregiver acknowledges the occurrence of a risk situation of the patient.

Since the device was designed as a very small apparatus, it could easily fall off the user's hand or foot. Hence, a glove in different sizes was designed, having a cap to contain the device inside while the user is wearing it. This cap is fixed to the glove with Velcro® and may be placed on any finger. The glove and the cap are made of elastic fabric and the cap has a transparent area made of plastic and/or porous material, such as PVC or the like, to allow seeing the display on the device. The glove may vary according to the user's hand size. It should be mentioned that the cap designed for newborns or infants could be especial: its end could hold a rubber or silicone pacifier attached to it, which may be flavored, so that the child may suck it while wearing the device (not shown in the figures).

The device might also comprise a temperature sensor and, if the user's body temperature is above a predetermined threshold, an alarm signal is sent to the remote communicated device. However, the temperature sensor can be disabled by the user.

Complex Algorithm

Figure 2:
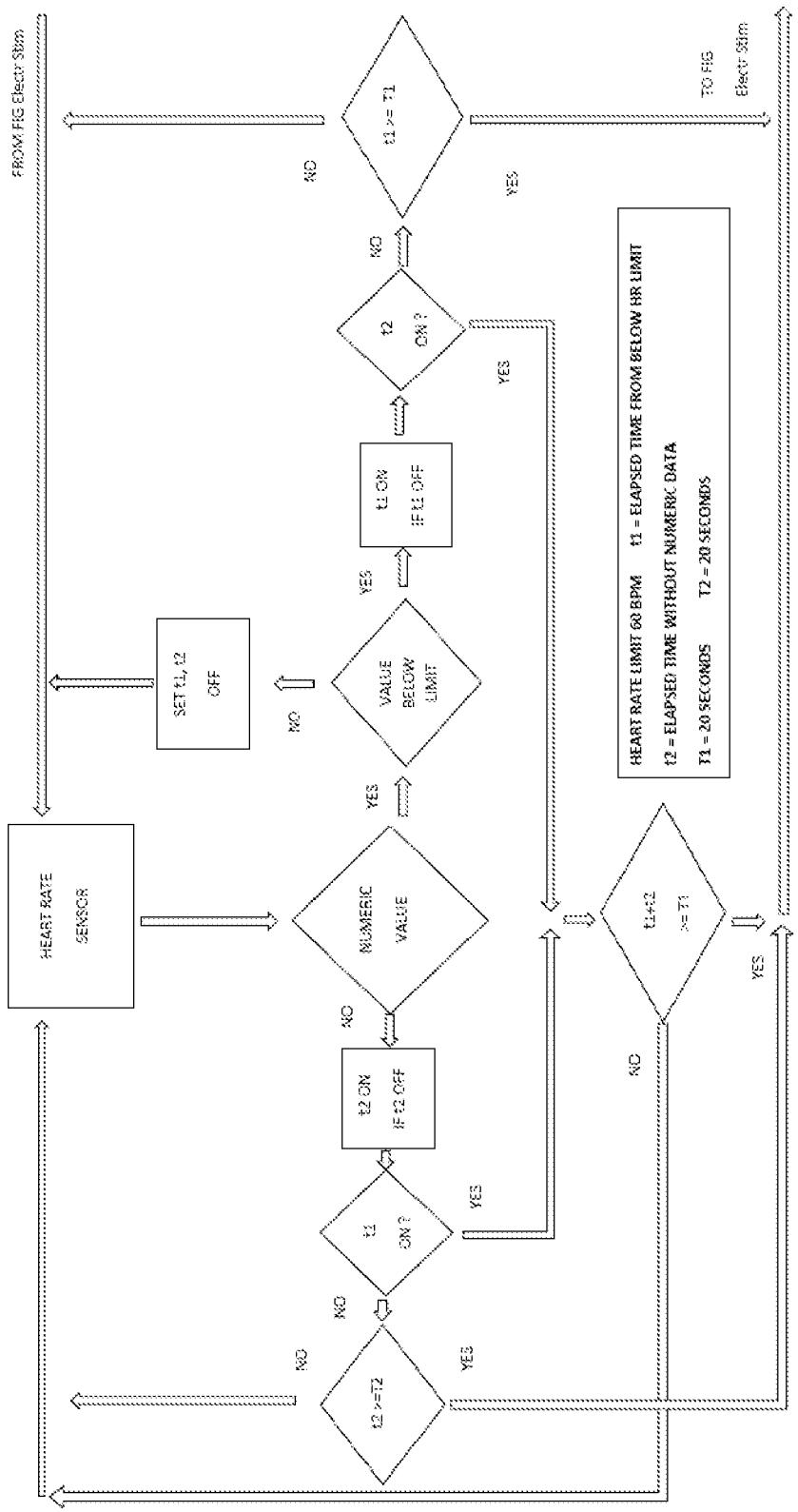
FIG. 2 is the Heart Rate part of the algorithm used by the device of the present invention, located in the microprocessor.
Figure 3:
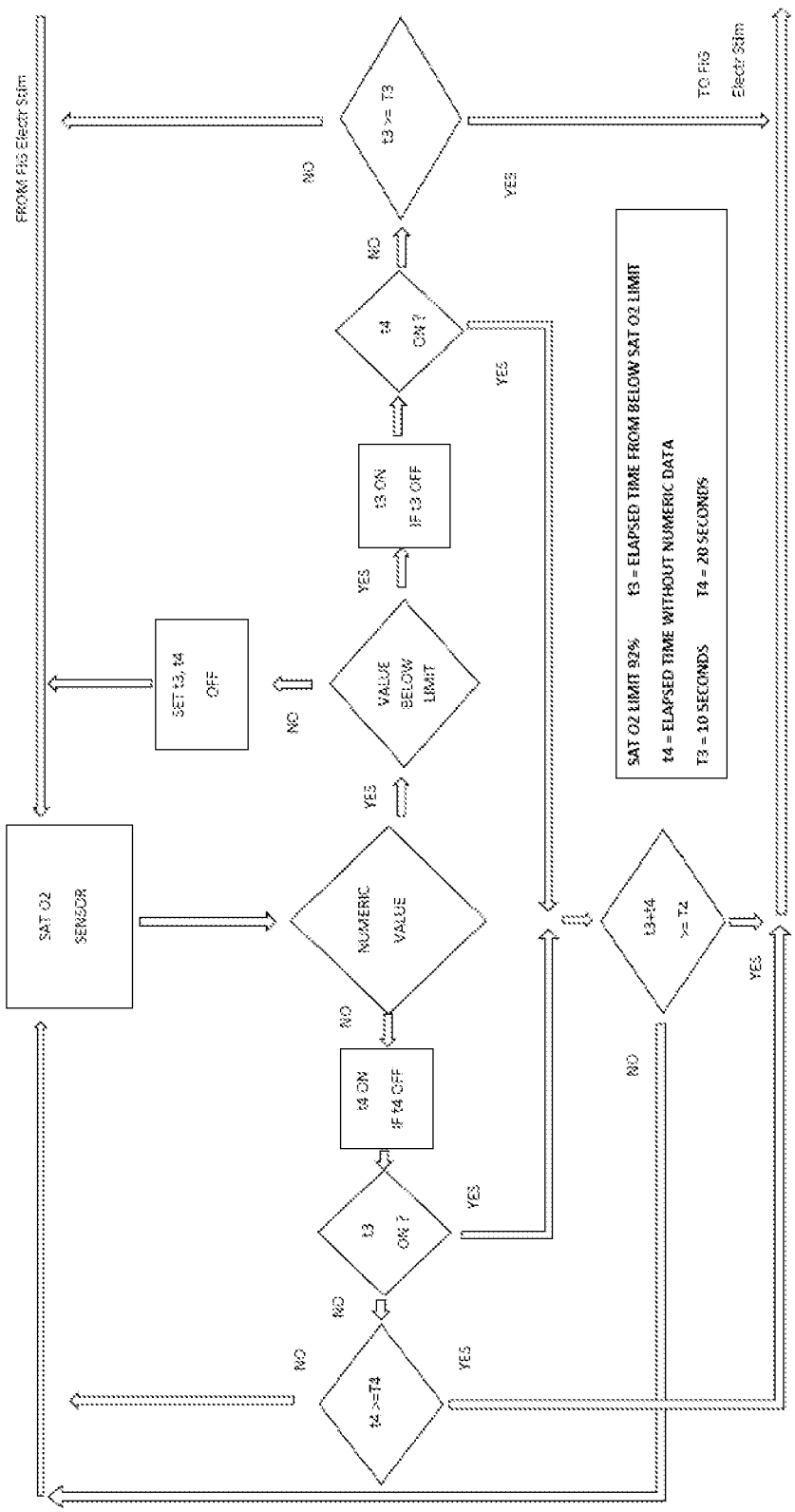
FIG. 3 is the Oxygen Saturation part of the algorithm used by the device of the present invention, located in the microprocessor.
Figure 4:
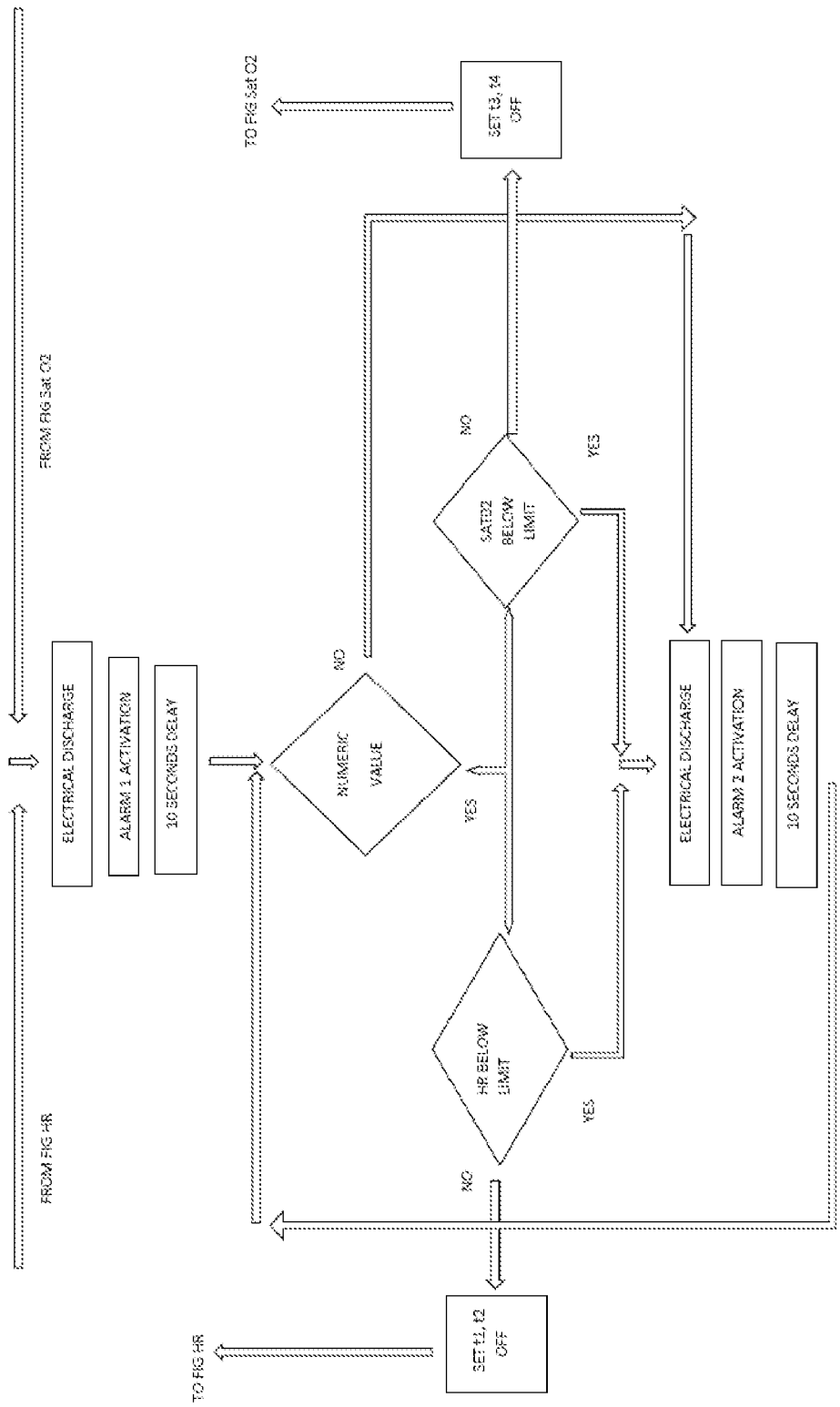
FIG. 4 is the electrical stimulus part of the algorithm used by the device of the present invention, located in the microprocessor.

Several checking routines correspond to the following usage scenarios (FIGS. 2, 3 and 4):

1. The device detects a heart rate value below the predetermined limit.

The timer 1 (t1) turns on. It checks the correct operation or placement of the device by checking if the timer 2 (t2) is turned on. If not, it checks if the first lapsed time (t1) is equal to, or higher than, time limit 1 (T1). If not, it returns to the heart rate measurement block. If this situation continues until the first lapsed time (t1) is equal, or higher than first time limit T1, it will deliver the stimulation signal to the user.

2. The device does not detect valid numeric heart rate data values.

This may be caused by malfunctions of the electronics of the corresponding measuring block or an unwanted misplacement of the device on the user's body.

The timer 2 (t2) is turned ON. It checks the user's health condition by checking if the timer 1 (t1) turned on. If not, it checks if second lapsed time (t2) is equal to, or higher than, time limit 2 (T2). If it is not verified, it returns to the heart rate measurement block. If this situation continues until the second lapsed time (t2) is equal to, or higher than the second time limit T2, it will deliver the stimulation signal to the user.

If in one of the above described situations the device detects that both timers t1 and t2 are active, it will check if the first lapsed time t1 plus the second lapsed time t2 is equal or higher than T1. If it is confirmed, it will deliver electrical stimulation to the user. If it is not verified, it will return to the heart rate measurement block.

3. The device detects blood oxygen saturation values below the predetermined limit.

The timer 3 (t3) is turned ON. It checks again the device's measuring condition or correct placement by checking if the timer 4 (t4) is turned on. If not, it checks if the third lapsed time (t3) is equal or higher than the third time limit 3 (T3). If it is not verified, it returns to the oxygen saturation measurement block. If this situation continues until the third lapsed time t3 is equal or higher than the third time limit T3, it will deliver the stimulation signal to the user.

4. The device does not detect numeric blood oxygen saturation valid data.

This may also be caused by malfunctions of the electronics of the corresponding measuring block or an unwanted misplacement of the device on the user's body.

The timer 4 (t4) is turned ON. It checks the user's health condition by checking if the timer 3 (t3) is turned on. If not verified, it checks if (t4) is equal to, or higher, than time 4 (T4). If it is not verified, it returns to the oxygen saturation measurement block. If this situation continues until t4 is equal to, or higher than T4, it will deliver the stimulation signal to the user.

If one of these previous situations of points 3 and 4 detects that both timers are active, it will check if t3 plus t4 is equal to, or higher than, T3. If this is confirmed, the device will deliver stimulation. If it is not verified, it will return to the oxygen saturation measurement block.

After delivering the first electrical discharge, the algorithm will wait 10 seconds and check if there is a numeric value. If it is confirmed, it will check if the heart rate or the oximetry values are below limit. If it is confirmed, the device will deliver the second electrical stimulation. If it is not confirmed, the device will turn off the timers (depending on the situation, it might choose to turn off t1 and t2, or t3 and t4).

After delivering the first electrical discharge, the algorithm will wait 10 seconds and checks if the measurement blocks are working correctly and for this it checks if any values are measured at all, and if no value is detected, it will deliver the second electrical stimulation as a preventive action.

From the second stimulation onwards and the following ones, the discharge current will be increasing (always in safe modes) and this was designed in this way foreseeing that it has been statistically found that most patients might keep alive 2 or 3 minutes before heart rate and blood oxygenation levels go below a dangerous level.

The caregiver can determine if he wants to receive an alarm either from the first time the baby receives his first stimulation or from the first minute.

Recommended Values:

SpO2 limit: 92%.

Heart Rate limit: 60 bpm.

T1, T2 and T4: 20 seconds.

T3: 10 seconds (it is extremely dangerous for the user if numeric values for blood oxygen saturation below the limit are continuously detected).

The complex algorithm of the present invention was designed to minimize delivering false alarms. It is known that in many situations healthy babies might suffer bradycardia (low heart rate from normal threshold) during sleeping periods, but under normal situations these should never happen for extended periods of time. To avoid this, the timers could be set in a range of 1 second to 30 seconds, and preferably set in 1 second if the users are adults.

When first used, the caregiver will be able to adjust the current amperage to be delivered to his child. When the device is placed on his child in his first sleep it may start delivering him/her electrical stimulation starting from the minimum amount and adding amperage until the caregiver sees his child reacts to the stimulation. In this way the device will be ready to be used. The caregiver could repeat this procedure once a month to be sure that his child reacts to the electrical stimulus.

The device was designed to allow the caregiver to turn the device on, off or set in stand by, when it is on the wearer. The baby might start crying after receiving the stimulation and, from that moment onwards, the false alarms might increase due to the baby's movements. The caregiver will be able to turn it off wirelessly from his smartphone or computer, or after reaching the baby and pressing the device's power on/off button.

The device might be supplied with factory settings which are the result of clinical studies and tests, but it can also be adjusted by the caregiver by means of a wireless remotely connected device or alternatively by a wired remote device to adjust the following parameters:

Sat O2 limit.

Heart rate limit.

Timers T1, T2, T3 and T4.

Amount of amperage to deliver.

Ability to set first, second or third stimulus deliverance before sending alarms to the caregiver.

When the device is placed on the baby, the caregiver can set a device activation delay to ensure baby is asleep before activating the device for stimuli deliverance.

The caregiver can turn on/off the device or place it in Stand By mode, whenever it is required, especially if the baby is crying.

Wireless on/off connection.

LED light with dimmer, or light on/off.

Ability to select from different wireless connections (Wifi, Bluetooth, smartphone) and to turn the device on/off.

After having sent a maximum of 18 stimuli or if the device has sent stimuli for 3 minutes, the device will turn on Stand By mode for 30 minutes.

Ability to send higher current of stimulus after the first sent stimulus.

Cloud gathering info on/off.

Ability to send a manual stimulus whenever the caregiver wants to test the reaction of the baby.

The device was designed for being used by virtually every infant, and particularly by: preterm babies, newborns and infants whose parents or caregivers wish to feel safer through its use; neonatal care units in hospitals, homes with family histories of sudden infant death syndrome.

Again, the main goal of the algorithm of the present invention is to minimize false alarms in pulse oximeter-based portable devices, and also, to avoid waking up babies during normal sleeping periods under normal bradycardias, based on the fact that, sometimes, healthy babies can have bradycardia during sleeping periods but, in normal situations those heart rate disturbances should never persist for more than 10-20 seconds.

U.S. Pat. No. 8,620,448 describes:

"At the time of an oxygen desaturation below a predetermined limit, or at the time of a drop in heart rate, a signal is triggered to the electric stimulation generator block 10, which delivers an electric stimulus to the finger skin through the two electrodes 6 placed on both sides of the sensor 1 detecting the oxygen saturation signal."

However, the device of the present invention, when the oxygen desaturation is below a predetermined limit, or when there is a drop in heart rate, does not send a stimulation immediately after the preset limit values are trespassed. Instead, a novel algorithm is activated, so the electrical stimulation will take effect only after the required checks are duly carried out.

The algorithm of the present invention can also be applied to enhance the device designed to avoid Sudden Infant Death Syndrome, described and claimed in U.S. Pat. No. 8,620,448. It is vital in this type of devices, as well as any other similar ones sold all over the world, to minimize any possible false alarms and this may be achieved with the algorithm of the present invention.

The present invention also comprises a method of reducing false alarms in a wearable pulse-oximeter-based device applicable to the hand or foot of a user, the device designed to measure blood oxygen saturation and heart rate values and intended to reduce critical situations of hypoxia and/or bradycardia that may happen in SIDS episodes, the device designed to deliver electrical stimulus to the user with a timing pattern and an intensity pattern in order to cause a reaction of the user in any of the following situations: a) the device stops measuring heart rate values or blood oxygen saturation values, b) the heart rate measurement generates values below a first corresponding predefined limit level, or c) the blood oxygen saturation measurement generates values below a second predefined limit level, The method comprising the reception of said blood oxygen saturation and heart rate values and, based on user predefined parameters and a programmed flow chart, carrying out checking routines to verify the correct placement of the device on the user's body and the normal operation of the device and setting adequate delays in the device's stimulus deliverance when measuring low heart rate or blood oxygen saturation values.

In a preferred embodiment, the method of the present invention comprises the steps of:

measuring a first lapsed time (t1) by means of a first timer (t1) from the moment said heart rate measurements fall below said first user-settable limit, said first lapsed time (t1) being related to a first predefined time limit (T1), and measuring a second lapsed time (t2) by means of a second timer (t2) from the moment said sensor stops measuring any heart rate values at all, said second lapsed time (t2) related to a second predefined time limit (T2);

measuring a third lapsed time (t3) by means of a third timer (t3) from the moment said blood oxygen saturation measurements falls below said second user-settable limit, said third lapsed time (t3) being related to a third predefined time limit (T3), and measuring a fourth lapsed time (t4) by means of a fourth timer (t4) from the moment said sensor stops measuring any blood oxygen saturation values at all, said fourth lapsed time (t4) being related to a fourth predefined time limit (T4).

In another preferred embodiment of the method of the present invention:

if the device does not measure any heart rate value at all and if the second timer (t2) is OFF, it turns the second timer (t2) ON and checks if the first timer (t1) is also ON; if the first timer (t1) is not ON, it checks if the second lapsed time (t2) reached the second time limit (T2);

if the second lapsed time (t2) did not reach the second time limit (T2) yet, the device returns to the step of measuring the heart rate; but if the second lapsed time (t2) reached the second time limit (T2), the device will deliver an electrical stimulus to the user;

if the device does not measure any heart rate value at all and if the second timer (t2) is OFF, it turns the second timer (t2) ON and checks if the first timer (t1) is also ON; if the first timer (t1) is ON, it adds the first and second lapsed times (t1+t2) of the first (t1) and second timer (t2);

if the resulting value of adding both lapsed times (t1+t2) is equal or greater than the first time limit (T1) of the first timer (t1), it will deliver an electrical stimulus to the user; but if the resulting value of adding both first and second lapsed times (t1+t2) is smaller than the first time limit (T1) of the first lapsed time (t1), the device returns to the step of measuring the heart rate again In another preferred embodiment of the method of the present invention:

if the device measures heart rate values, it checks if the measured heart rate value is below its predetermined limit, and if this is not verified, it turns both first and second timers (t1, t2) OFF and the device returns to the step of measuring the heart rate again;

if the device measures heart rate values, it checks if the measured heart rate value is below its predetermined limit, and if this is confirmed, the first timer (t1) is turned ON and the algorithm checks the correct operation of the device by checking if the second timer (t2) is turned ON; if the second timer (t2) is OFF, the device checks if the first lapsed time of the first timer (t1) is equal or greater than its first time limit T1; if this is not verified, the device turns back to the step of measuring heart rate; if the first lapsed time of the first timer (t1) reached the first time limit (T1), the device will deliver an electrical stimulus to the user;

if the device measures heart rate values, it checks if the measured heart rate value is below its predetermined limit, and if this is verified, the first timer (t1) is turned ON and the algorithm checks the correct operation of the device by checking if the second timer (t2) is turned ON, the first lapsed time of the first timer (t1) is added to the second lapsed time of the second timer t2;

if the resulting value of adding both first and second lapsed times (t1+t2) is equal or greater than the first time setting T1 of the first timer (t1), it will deliver an electrical stimulus to the user; but if the resulting value of adding both first and second lapsed times (t1+t2) is smaller than the first time setting T1 of the first timer (t1), the device returns to the step of measuring the heart rate.

In another preferred embodiment of the method of the present invention:

if the device does not measure any blood oxygen saturation value at all and if the fourth timer (t4) is OFF, it turns the fourth timer (t4) ON and checks if the third timer (t3) is also ON; if the third timer (t3) is not ON, it checks if the fourth lapsed time (t4) of the fourth timer (t4) reached the fourth time limit (T4); if the fourth lapsed time (t4) of the fourth timer (t4) did not reach the fourth time limit (T4) yet, the device returns to the step of measuring the blood oxygen saturation; but if the fourth lapsed time of the fourth timer (t4) reached the fourth time limit (T4), the device will deliver an electrical stimulus to the user;

if the device does not measure any blood oxygen saturation value at all and if the fourth timer (t4) is OFF, it turns the fourth timer (t4) ON and checks if the third timer (t3) is also ON; if the third timer (t3) is ON, the third lapsed time of the third timer (t3) is added to the fourth lapsed time (t4) of the fourth timer (t4) and, if the resulting value of adding both third and fourth lapsed times (t3+t4) is equal or greater than the third time limit (T3) of the third timer (t3), it will deliver an electrical stimulus to the user, but if the resulting value of adding both third and fourth lapsed times (t3+t4) is smaller than the third time limit (T3) of the third timer (t3), the device returns to the step of measuring the blood oxygen saturation.

In another preferred embodiment of the method of the present invention:

if the device measures blood oxygen saturation values, it checks if the measured blood oxygen saturation value is below its predetermined limit, and if this is not verified, it turns both third and fourth timers (t3, t4) OFF and the device returns to the step of measuring the blood oxygen saturation;

if the device measures blood oxygen saturation values, it checks if the measured blood oxygen saturation value is below its predetermined limit, and if this is confirmed, the third timer (t3) is turned ON and the algorithm checks the correct operation of the device by checking if the fourth timer (t4) is turned ON; if the fourth timer (t4) is OFF, the device checks if the third lapsed time of the third timer (t3) is equal or greater than its third time limit T3; if this is not verified, the device turns back to the step of measuring blood oxygen saturation; if the third lapsed time of the third timer (t3) reached the third time limit (T3), the device will deliver an electrical stimulus to the user;

if the device measures blood oxygen values, it checks if the measured blood oxygen saturation value is below its predetermined limit, and if this is verified, the third timer (t3) is turned ON and the algorithm checks the correct operation of the device by checking if the fourth timer (t4) is turned ON, the third lapsed time of the third timer (t3) is added to the fourth lapsed time (t4) of the fourth timer (t4);

if the resulting value of adding both third and fourth lapsed times (t3+t4) is equal or greater than the first time setting T3 of the first timer (t3), it will deliver an electrical stimulus to the user; but if the resulting value of adding both lapsed times (t3+t4) is smaller than the first time setting T3 of the first timer (t3), the device returns to the step of measuring the blood oxygen saturation.

In another preferred embodiment of the method of the present invention:

after delivering the first electrical stimulus, the device will send out a first alarm and wait 10 seconds, and check if a heart rate value or a blood oxygen saturation value was measured;

if it is not confirmed, the device will deliver an electrical stimulus to the user; it activates the second timer and waits another 10 seconds before checking again the existence of a measured heart rate value or a blood oxygen saturation value:

if the measurement of a heart rate value or a blood oxygen saturation value is confirmed, it will check if the heart rate is below its safe limit and if the blood oxygen saturation value is also below its safe limit; if any of these situations are confirmed, the device will deliver the second electrical stimulation, send out a second alarm and return to the measurement of a heart rate value or a blood oxygen saturation value.

In another preferred embodiment of the method of the present invention:

after the second stimulation the device, the device delivers further stimulus signals increasing the discharge current in preset current steps until reaching a maximum preset safety limit, wherein said safety limit is selected according to the age and weight of the user.

In the method of the present invention, the total stimulus signal current range is 0.01 mA to 5.0 mA and the maximum operation time is 3 minutes.

The method of the present invention comprises wirelessly transmitting alarms to devices selected form a group formed by smartphones, tablets, PCs and Internet interfaces communing to cloud services.

In a further embodiment, the method of the present invention comprises measuring human body temperature.

The foregoing disclosure has been set forth merely to illustrate the invention and is not intended to be limiting. Modifications of the disclosed embodiments incorporating the spirit and substance of the invention may occur to persons skilled in the art, and the invention should be construed to include everything within the scope of the invention ultimately claimed.

The invention claimed is:

1. A method of reducing false alarms in a wearable pulse-oximeter-based device applicable to a hand or a foot of a user, said device comprising (i) a pulse-oximeter sensor designed to measure and output blood oxygen saturation and heart rate values, intended to reduce critical situations of hypoxia and/or bradycardia that may happen in SIDS episodes, and designed to deliver electrical stimulus to the user with a timing pattern and an intensity pattern in order to cause a reaction of the user when a) said device stops measuring heart rate values or blood oxygen saturation values, b) heart rate measurement generates values below a first corresponding predefined limit level, or c) blood oxygen saturation measurement generates values below a second predefined limit level, (ii) a block section for housing elements forming the pulse-oximeter sensor comprising a blood oxygen saturation sensor and a heart rate meter, (iii) a measurement and display driver circuit, and (iv) a display; the device further comprising (v) a pair of electrodes designed for delivering current stimulus to the user, wherein the current stimulus is generated by an electrical stimulus generator, (vi) a control and alarm-generating circuit storing an algorithm, and (vii) a power supply, said method comprising:

receiving said blood oxygen saturation by said blood oxygen saturation sensor and said heart rate values by said heart rate meter in said block section, carrying out checking routines in said control and alarm-generating circuit, based on user predefined parameters and said algorithm, to verify correct placement of the device on the body of the user and a normal operation of the device and setting delays in the current stimulus delivered to the user when measuring low heart rate or blood oxygen saturation values to avoid false alarming, measuring a first lapsed time (t1), by way of a first timer, from a moment said heart rate measurements fall below a first user-settable limit, said first lapsed time (t1) having a first predefined time limit (T1), wherein the first timer stops measuring when t1=T1, measuring a second lapsed time (t2), by way of a second timer, from a moment said pulse-oximeter sensor is still operational but does not pick up any heart rate values and the measured heart rate is zero, said second lapsed time (t2) having a second predefined time limit (T2), wherein the second timer stops measuring when t2=T2, measuring a third lapsed time (t3), by way of a third timer, from a moment said blood oxygen saturation measurements fall below a second user-settable limit, said third lapsed time (t3) having a third predefined time limit (T3), wherein the third timer stops measuring when t3=T3, measuring a fourth lapsed time (t4) by ways of a fourth timer, from a moment said pulse-oximeter sensor is still operational but does not pick up any blood oxygen saturation values at all and the oxygen saturation is zero, said fourth lapsed time (t4) having a fourth predefined time limit (T4), wherein the fourth timer stops measuring when t4=T4, determining that the pulse-oximeter sensor is still operational but does not pick up any heart rate values, and determining that the pulse-oximeter sensor is still operational but does not pick up any blood oxygen saturation values at all.

2. The method according to claim 1, wherein:

the device measures blood oxygen saturation values, checks if the measured blood oxygen saturation value is below a predetermined limit, and if this is not verified, turns both of the third and fourth timers OFF, and measures again the blood oxygen saturation, the device measures blood oxygen saturation values, checks if the measured blood oxygen saturation value is below the predetermined limit, and, if this is confirmed, turns the third timer ON and checks with the algorithm for correct operation of the device by checking if the fourth timer is turned ON, if the fourth timer is OFF, checks if the third lapsed time (t3) of the third timer is equal or greater than its third time limit T3, and if this is not verified, the device measures again blood oxygen saturation, if the third lapsed time (t3) of the third timer is equal to the third time limit (T3), the device delivers an electrical stimulus to the user, if the fourth timer is turned ON, the third lapsed time (t3) of the third timer is added to the fourth lapsed time (t4) of the fourth timer, and if a value resulting from adding both the third and fourth lapsed times (t3+t4) is equal or greater than the fourth predefined time limit, the device delivers an electrical stimulus to the user and turns both the third and fourth timers OFF, but if the value resulting from adding both the third and fourth lapsed times (t3+t4) is smaller than the fourth predefined time limit (T4), the device measures again the blood oxygen saturation.

3. The method according to claim 2, wherein:

after delivering a first electrical stimulus, the device sends out a first alarm, waits 10 seconds, and checks if a heart rate value or a blood oxygen saturation value was measured, and, if the heart rate value or the blood oxygen saturation value was not measured, the device delivers a second electrical stimulus to the user, activates the second timer, and waits another 10 seconds before checking again for existence of a measured heart rate value or a blood oxygen saturation value, after delivering a first electrical stimulus, the device sends out a first alarm, waits 10 seconds, and checks of a heart rate value or a blood oxygen saturation value was measured, and, if a heart rate value or a blood oxygen saturation value was measured, the device checks if the heart rate is below a safe value and if the blood oxygen saturation value is also below a safe value, and, if any of these situations are confirmed, the device delivers a second electrical stimulation, sends out a second alarm, and returns to measurement of a heart rate value or a blood oxygen saturation value.

4. The method according to claim 3, wherein:

after the second electrical stimulation, the device delivers further stimulus signals increasing a discharge current in preset current steps until reaching a maximum preset safety limit, and said safety limit is selected according to an age and a weight of the user.

5. The method according to claim 4, wherein a total stimulus signal current range is 0.01 mA to 5.0 mA, and a maximum operation time is 3 minutes.

6. The method according to claim 1, further comprising wirelessly transmitting alarms to devices selected from a group formed by smartphones, tablets, PCs, and Internet interfaces communicating with cloud services.

7. The method according to claim 1, further comprising measuring human body temperature.

8. The method according to claim 1, wherein the device is housed in a ring in which the electrical stimulus is delivered to a finger of the user, or housed in a hand glove in which the electrical stimulus is delivered to a hand palm, or housed in a foot bootie in which the electrical stimulus is delivered to a foot plant, or housed in a wrist band in which the electrical stimulus is delivered to a user's wrist.

* * * * *